United States Patent [19]
Maitz et al.

[11] Patent Number: 6,031,929
[45] Date of Patent: Feb. 29, 2000

[54] IMAGE FACSIMILE WITH REAL TIME IMAGE SEGMENTATION

[75] Inventors: Glenn S. Maitz; Walter F. Good, both of Pittsburgh; John M. Herron, Gibsonia; David Gur, Pittsburgh, all of Pa.

[73] Assignee: University of Pittsburgh, Pittsburgh, Pa.

[21] Appl. No.: 08/683,314

[22] Filed: Jul. 18, 1996

[51] Int. Cl.$^7$ ..................................................... G06K 9/00
[52] U.S. Cl. ......................... 382/132; 382/173; 382/232; 382/251
[58] Field of Search ................................... 382/132, 250, 382/251, 100, 173, 232, 164, 174–180; 358/400, 401, 508, 539

[56] References Cited

U.S. PATENT DOCUMENTS

| | | | |
|---|---|---|---|
| 4,558,462 | 12/1985 | Horiba et al. | 382/42 |
| 4,774,574 | 9/1988 | Daly et al. | 358/133 |
| 5,646,997 | 7/1997 | Barton | 380/23 |
| 5,694,484 | 12/1997 | Cottrell et al. | 382/100 |
| 5,710,590 | 1/1998 | Ichige et al. | 348/14 |
| 5,748,173 | 5/1998 | Gur | 345/115 |
| 5,815,591 | 9/1998 | Roehrig et al. | 382/130 |

OTHER PUBLICATIONS

Walter S. Kuklinski, et al, Application of Fractal Texture Analysis to Segmentation of Dental Radiographs, SPIE vol. 1092 Medical Imaging III: Image Processing (1989), pp. 111–117.

Heidi A. Peterson, et al, Image Segmentation Using Human Visual System Properties with Applications in Image Compression, SPIE vol. 1077 Human Vision, Visual Processing, and Digital Display (1989), pp. 155–163.

Ewa Pietka, Lung Segmentation in Digital Radiographs, Journal of Digital Imaging, vol. 7, No. 2 (May), 1994, pp. 79–84.

Kyongtae T. Bae, et al, Automatic Segmentation of Liver Structure in CT Images, Med. Phys. 20(1), Jan./Feb. 1993, pp. 71–78.

J.C. Bezdek, et al, Review of MR Image Segmentation Techniques Using Pattern Recognition, Med. Phys. 20(4), Jul./Aug. 1993.

Walter F. Good, et al, Joint Photographic Experts Group (JPEG) Compatible Data Compression on Mammograms, Journal of Digital Imaging, vol. 7, No. 3 (Aug.), 1994, pp. 123–132.

*Primary Examiner*—Phuoc Tran
*Attorney, Agent, or Firm*—IP Group of Pillsburry Madison & Sutro LLP

[57] ABSTRACT

A method and system for remote diagnosis of a radiograph includes remote locations connectable to diagnosis locations. At a remote location a radiographic image containing a part depicting tissue and a background part is obtained and digitized. The image can be considered to comprise a plurality of blocks. A block of the digitized radiographic image is segmented to obtain a part of the block which depicts mainly tissue. The part of the block is compressed and transmitted to a diagnosis location. This segmenting, compressing and transmitting of blocks is repeated until the entire part of the image which depicts tissue has been transmitted to the diagnosis location. For an image, the digitization, segmentation, compression and transmission can be performed in a pipelined fashion. optionally computer assisted diagnosis (CAD) can be performed on the digitized image. The diagnosis location receives the compressed segmented image and any CAD results; uncompressing the received image; combining the CAD results with the uncompressed image; and displays the uncompressed image and the CAD results.

56 Claims, 13 Drawing Sheets

IMAGE FACSIMILE WITH REAL TIME IMAGE SEGMENTATION

FIELD OF THE INVENTION

This invention relates to teleradiology, and, more particularly, to teleradiology of mammograms using real-time, on-the-fly image segmentation.

BACKGROUND OF THE INVENTION

Teleradiology is the process of sending radiologic images from one point to another through digital, computer-assisted transmission, typically over standard telephone lines (POTS), or over a wide-area network (WAN) using dial-up ISDN lines or other switched digital services. Using teleradiology, images can be sent from one part of a hospital to another part of the same hospital, from one hospital to another, from remote sites to diagnostic centers, etc. In other words, images obtained at one location can be sent to almost any place in the world.

As cost-effectiveness in medical diagnostic imaging becomes a major issue, teleradiology (remote radiology or the transmission of radiologic images) is becoming an acceptable way to make diagnoses and to consult with referring physicians. Teleradiology has been called the "great equalizer for radiology" and it has allowed normal practice limitations like distance, licensure and reimbursement to be largely eliminated. Computer-assisted transfer of digitized images allows geographically dispersed consultants to lend their expertise to remote regions, thereby benefiting patients who now may have limited access to radiological services. Teleradiology systems especially are important to rural medical facilities.

Teleradiology requires trade-offs of image quality (that is, image quality sufficient to perform accurate diagnosis) with system cost and image transmission time.

Although some teleradiology systems have been implemented using standard, off-the-shelf equipment, effective teleradiology typically requires expensive, specialized equipment as well as persons trained in its operation, maintenance and use. As a consequence, in remote locations where teleradiology would be of most use, it is unlikely to be readily available. As noted in a recent article on the subject, "[a]lthough technological advances continue to drive decreases in system prices, teleradiology and telemedicine continue to face significant challenges." 17/2 *Health Management Technology* Feb. 22, 1996.

Low-cost teleradiology systems developed using standard, off-the-shelf components suffer from various problems. For example, in one system "the image digitization time . . . was quite long." *Low cost digital teleradiology*, Reponen J. et al, 19/3 EUR. J. RADIOL. 226–231, 1995.

Radiographic images (X-rays) typically contain vast amounts of information. It is therefore desirable to be able to compress the images, especially in a teleradiology system where the images are to be electronically transferred to remote locations in a reasonable amount of time.

In many radiographic images, areas which do not depict tissue or other regions of interest (ROI) may be eliminated to reduce the amount of data managed by systems and transferred between systems. Segmentation or partitioning of an image may also enable more efficient data compression of the image. Segmentation schemes using complete images have been used.

In the specific area of telemammography, results have been mixed. One study concluded that further improvements in hardware and imaging parameters may improve detection of soft tissue abnormalities and that further evaluation is necessary to determine whether teleradiology might be applicable to breast cancer screening. *Detection of breast abnormalities on teleradiology transmitted mammograms*, Fajardo L. L. et al., 25/10 INVEST. RADIOL. 1111–1115, 1990.

It is therefore desirable and useful to provide teleradiology for mammograms which achieves a good balance of the quality/cost/time trade-off. That is, it is desirable to provide teleradiology for mammograms using standard imaging, computer and communication equipment while still achieving acceptable results.

It is also desirable to segment images in real-time (or almost real-time) as they are obtained from an image acquisition system (for example, a film digitizer).

SUMMARY OF THE INVENTION

In one aspect, this invention is a teleradiology system which overcomes problems with the above-mentioned systems by providing a low-cost teleradiology system which produces high-quality images in almost real time.

In another aspect, this invention provides two independent image segmentation schemes to segment images from a limited data set. The two schemes can be used in combination to compare results and improve reliability.

These segmentation schemes are able to operate in real-time (or almost real-time), segmenting images obtained from an acquisition system based on a limited amount of information such as eight lines or columns of image data.

In one aspect, this invention is a method for remote diagnosis of a radiograph. The method includes, at a remote location: obtaining and digitizing a radiographic image containing a part depicting tissue and a background part, wherein the image can be considered to comprise a plurality of blocks; segmenting a block of the digitized radiographic image to obtain a part of the block which depicts mainly tissue; compressing and transmitting the part of the block to a diagnosis location; and repeating the segmenting, compressing and transmitting of blocks until the entire part of the image which depicts tissue has been transmitted to the diagnosis location.

In another preferred embodiment, the method further includes, at the remote location: optionally performing computer assisted diagnosis (CAD) on the digitized image; and transmitting the results of the CAD to the diagnosis location.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which.

DETAILED DESCRIPTION OF THE PRESENTLY PREFERRED EXEMPLARY EMBODIMENTS

Figure 1:
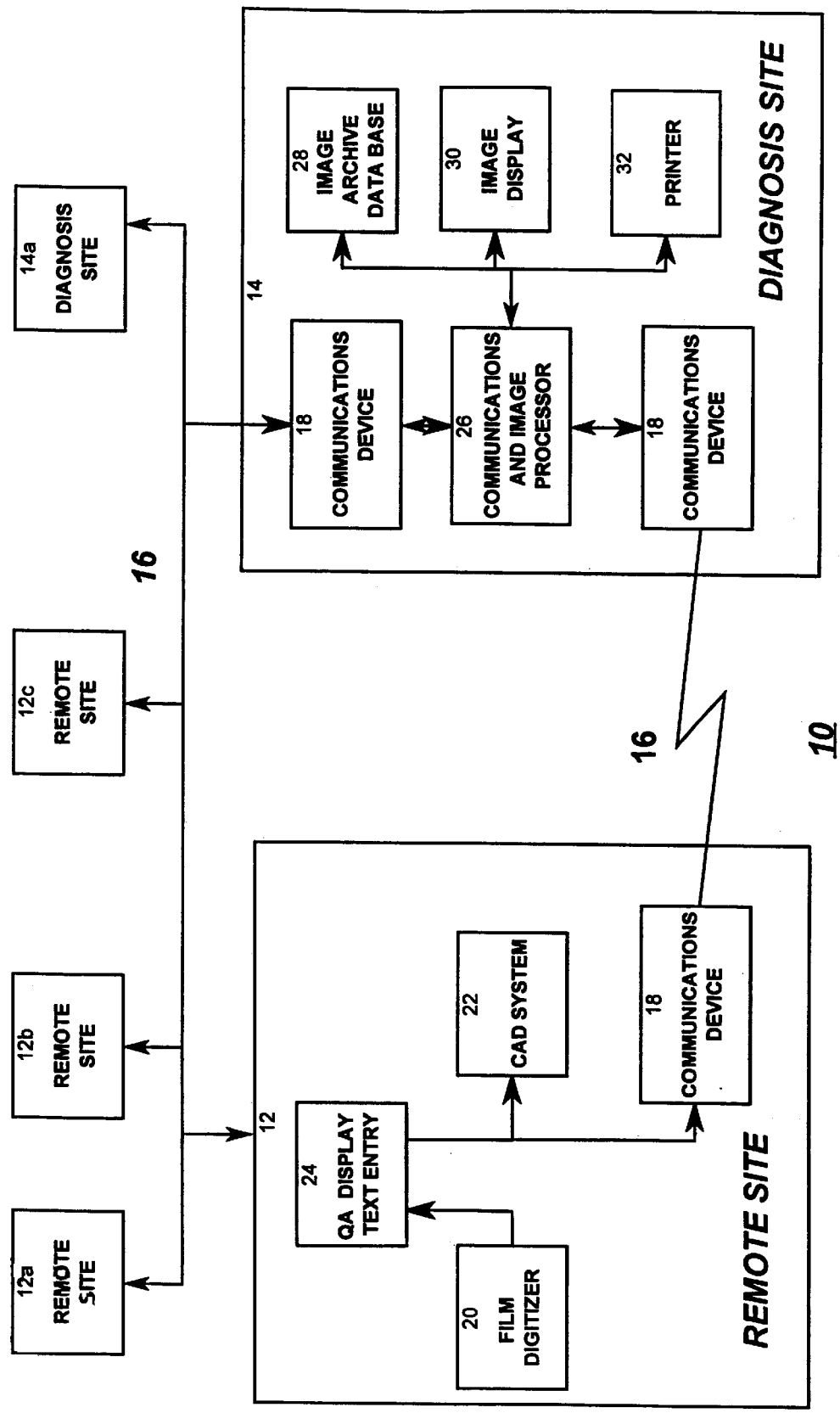
FIG. 1 depicts a teleradiology system of the present invention.

A teleradiology system 10 according to the present invention includes various sites, namely one or more remote sites 12 and one or more diagnosis sites 14. Each remote site 12 is connected to at least one diagnosis site 14 via communication channels 16. The network of sites can be a LAN or a WAN or communication over channels 16 can be performed by communications devices (e.g., bridges, modems and the like) 18, depending on the system configuration and the location of the sites. The network of sites can be any combination of LANs, WANs and other networks or communication links in which a remote site 12 can communicate with a diagnostic site 14.

A site may have more than one communications device 18. Practical implementation is through an integration of routing, bridging and switching functions. Typically a remote site 12 has one communications device such as a modem 18 and connects to a single diagnosis site whereas a diagnosis site 14 receives images from more than one remote site 12 using one or more modems.

Each remote site 12 includes a film digitizer 20 and a CAD system 22, both connected to a quality assurance (QA) display and text entry system 24. The CAD system 22 and the QA system 24 are connected to the site's communications device 18.

A diagnosis site 14 includes a communications and image processor 26 connected to an image archive database 28, and image display 30 and an output device such as a printer 32. The processor 26 is connected to the site's communications devices 18.

In presently preferred embodiments, at a remote site 12, the film digitizer 20 is a Lumisys FD 150 digitizing at 50 $\mu$m resolution during a 50 second process. The QA system 24 is a Gateway 2000 P5-90 with a 15 inch Vivitron monitor, and the modem is a Microcom Deskporte 28.8 Kbps modem or a Zyxel Elite 2864 28.8 Kbps modem.

At diagnosis sites 14, the communications device 18 is the same as at the remote sites (a 28.8 Kbps modem) and is compatible with remote communications devices 18. The printer is a Kodak HR 2180 laser printer capable of printing an image with a resolution of 43 $\mu$m.

Operation

Figure 2:
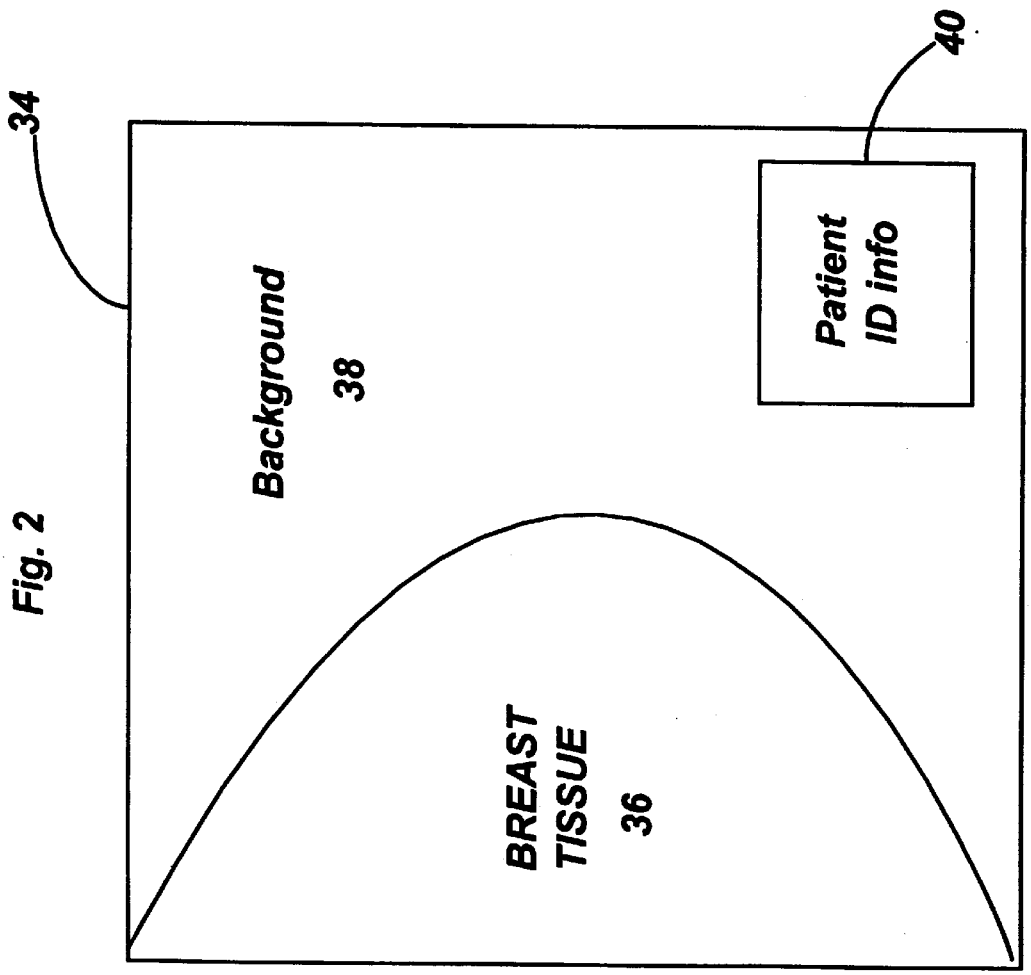
FIG. 2 shows a typical mammogram processed by the system of the present invention.

In presently preferred embodiments, the present invention operates on images such as the mammogram 34 of FIG. 2. Mammogram 34 consists essentially of three parts: a soft tissue part 36 depicting breast tissue, a background part 38, and patient identification information 40. The patient identification information 40 is typically added to the mammogram 34 at the time the image is formed or processed and is used to associate the mammogram with a particular patient. The information 40 can be, for example, textual, barcodes or combinations thereof.

Figure 3:
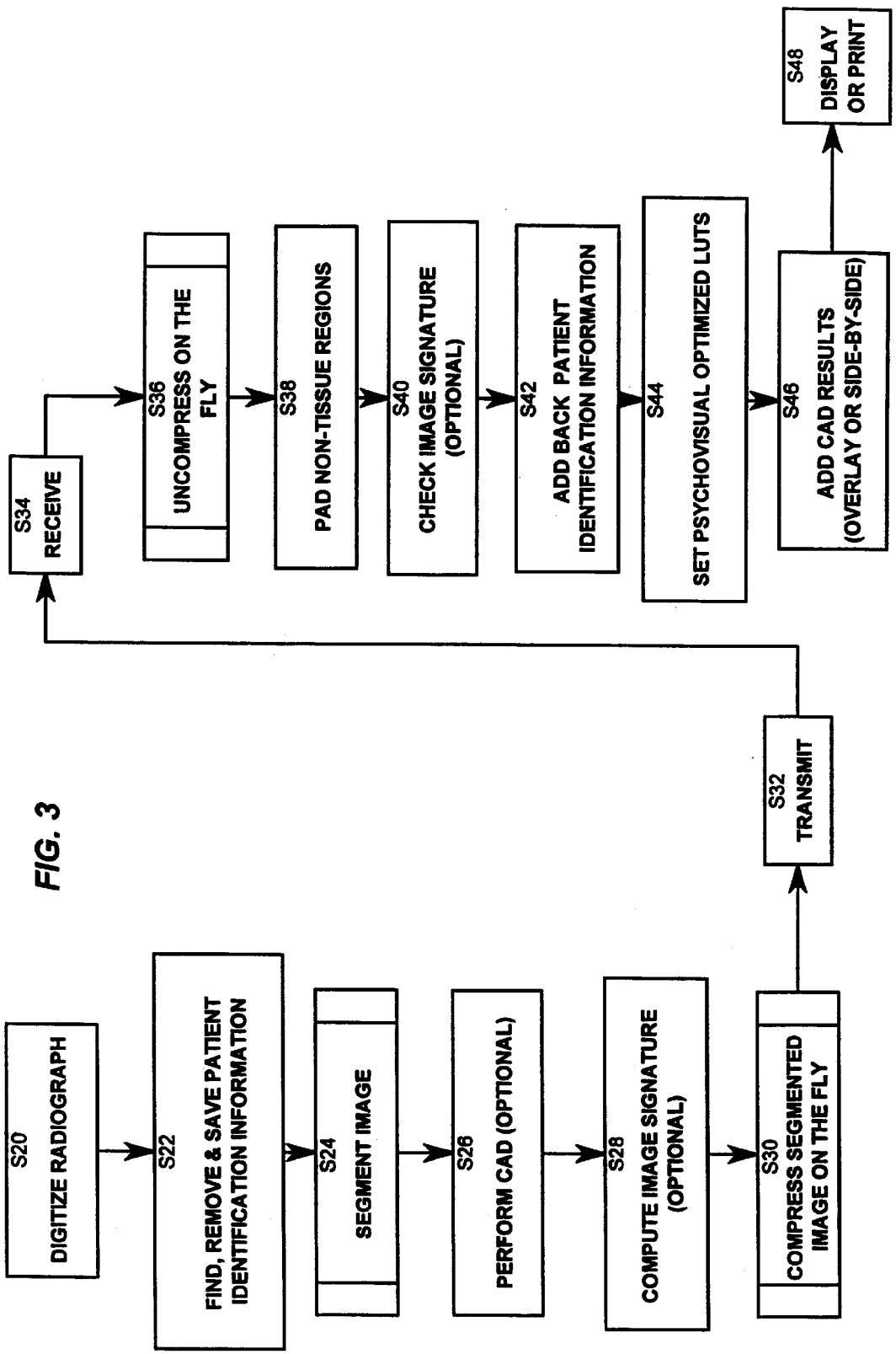
FIGS. 3 and 4 depict the flow of operation of the system of FIG. 1 on a typical mammogram as shown in FIG. 2.
Figure 4:
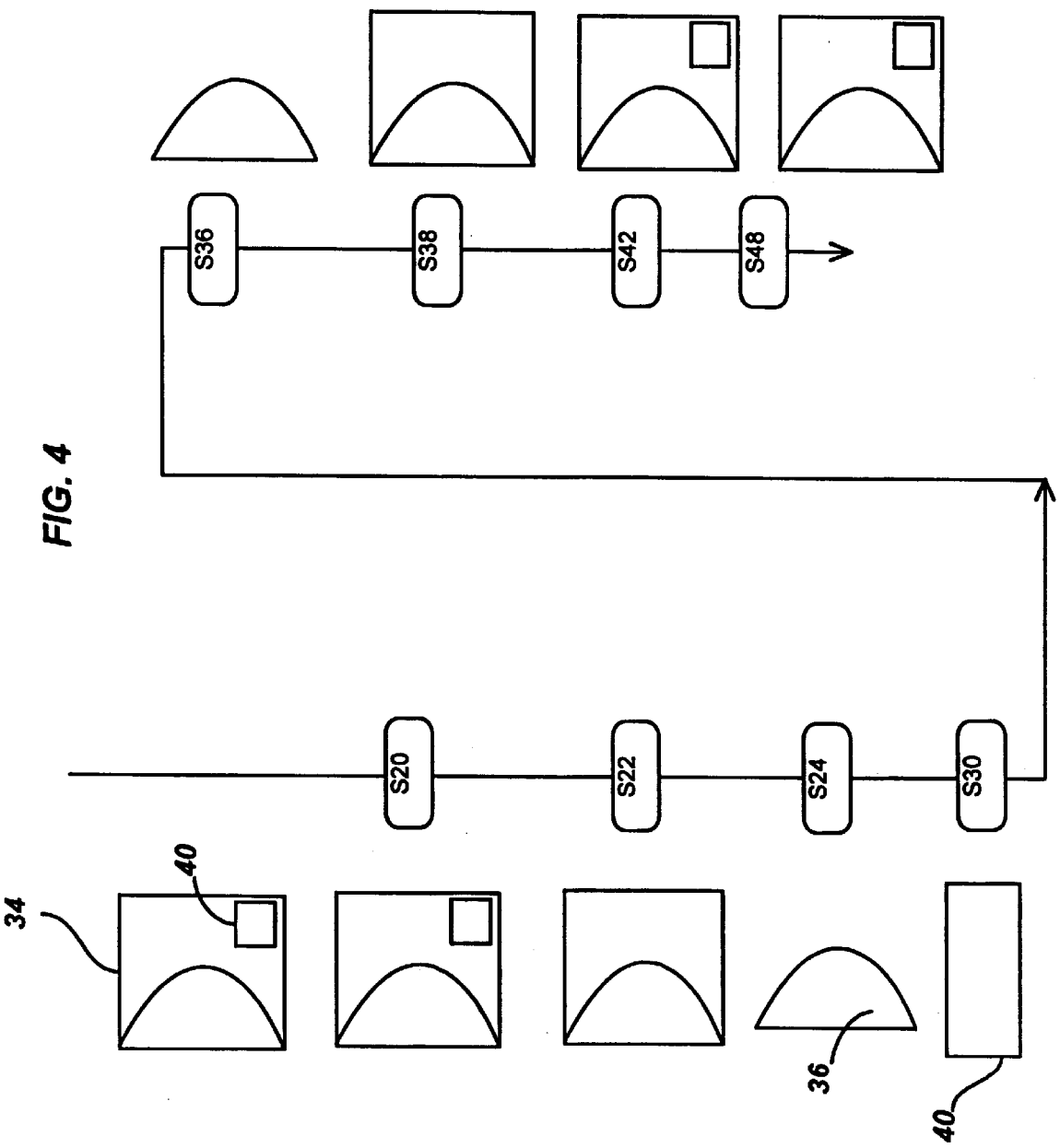

In operation, the system 10 works as follows (with reference to FIGS. 3 and 4):

A radiograph (e.g., mammogram 34 including patient identification information 40) is produced at a remote site 12 using some appropriate device (not shown). This radiograph is then digitized (step S20) using film digitizer 20 to produce a digital version of the radiograph which can then be checked for quality control by QA display and text entry system 24. Next the patient identification information 40 is found, removed from the image and saved (step S22). This finding and removal can be done by an operator or by a program which searches for the region.

A typical digitized mammogram comprises about forty megabytes (~40 MB) of data. The present digitizer takes about fifty (50) seconds to digitize an image.

Once the image has been digitized, processed by the QA system, and the identification information has been removed and saved, the image is then segmented by removing the non-tissue areas (step S24). The segmentation process is described in greater detail below and reduces a typical digital mammogram to between about five and fifteen megabytes of data.

The image can then optionally be subjected to computer aided diagnosis (using the CAD processor and display 22) (step S26). If CAD is performed, various so-called regions of interest (ROIs) are located on the digitized image. These correspond to regions which depict potential problems in the tissue or bone (hard tissue) depicted in the radiograph. For example, in the case of mammograms, the ROIs could depict masses or clusters of microcalcifications.

Presently preferred embodiments of this system 10 operate on digital mammograms. In these embodiments, the CAD scheme is one or more of the CAD schemes described in U.S. patent applications Ser. Nos. 08/352,169, 08/556,814 and 08/613,363, the entire contents of which are hereby incorporated herein by reference.

In some preferred embodiments, a digital signature of the segmented image and the patient identification information 40 is determined (step S28) and saved. Any well-known message digest algorithm or mechanism can be used to determine this digital signature.

The tissue region of the image is then compressed on the fly (step S30) and transmitted to a remote diagnosis site 14 (step S32). The process of on the fly compression is described in greater detail below. Compression of the tissue region reduces it to between about fifty to six hundred kilobytes (~50–600 KBytes). Transmission rates are about 2 KBytes/sec via POTS or faster by ISDN.

Once the image has been completely transmitted, the previously saved patient identification information 40 (saved in step S22) is sent along with any CAD results and signatures (if steps S26 and S28, respectively, are performed).

At the diagnosis site 14, the image, patient identification information and any other data (e.g., signatures and ROIs) are received (step S34), the image is uncompressed on the fly (step S36) and is padded to insert the non-tissue regions (step S38).

If a signature was determined at the remote site (step S28) then this signature is checked to ensure that the image and the patient information 40 match and are valid.

Next, the patient identification information 40 is added back into the image (step S42) and optimized lookup tables (described further below) are set (step S44). These tables match optimal densities in the original image at the remote locations with the final image as displayed or printed onto film to assure that the "look" and "feel" of the final image is the same as that of the original tissue portion of the image.

Finally the image is displayed on image display 30 (step S48) with the CAD results (if any are present) displayed by overlay or side-by-side with the image (steps S46). The image can also be printed on printer 32 and stored in the image archive database 28.

Figure 5:
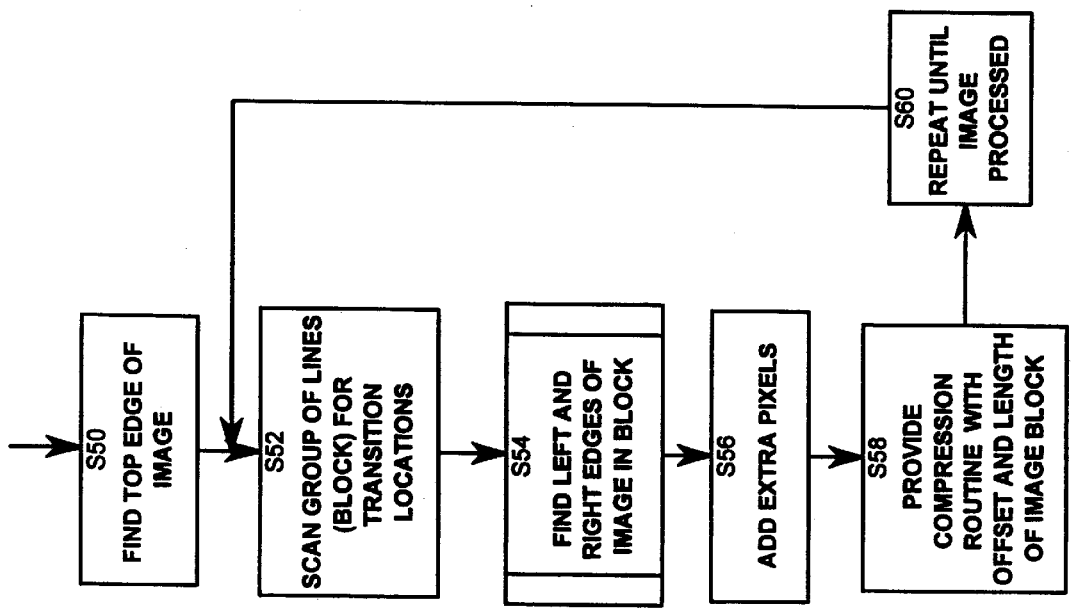
FIGS. 5 and 6 depict the flow of the real-time on-the-fly segmentation according to the present invention.
Figure 6:
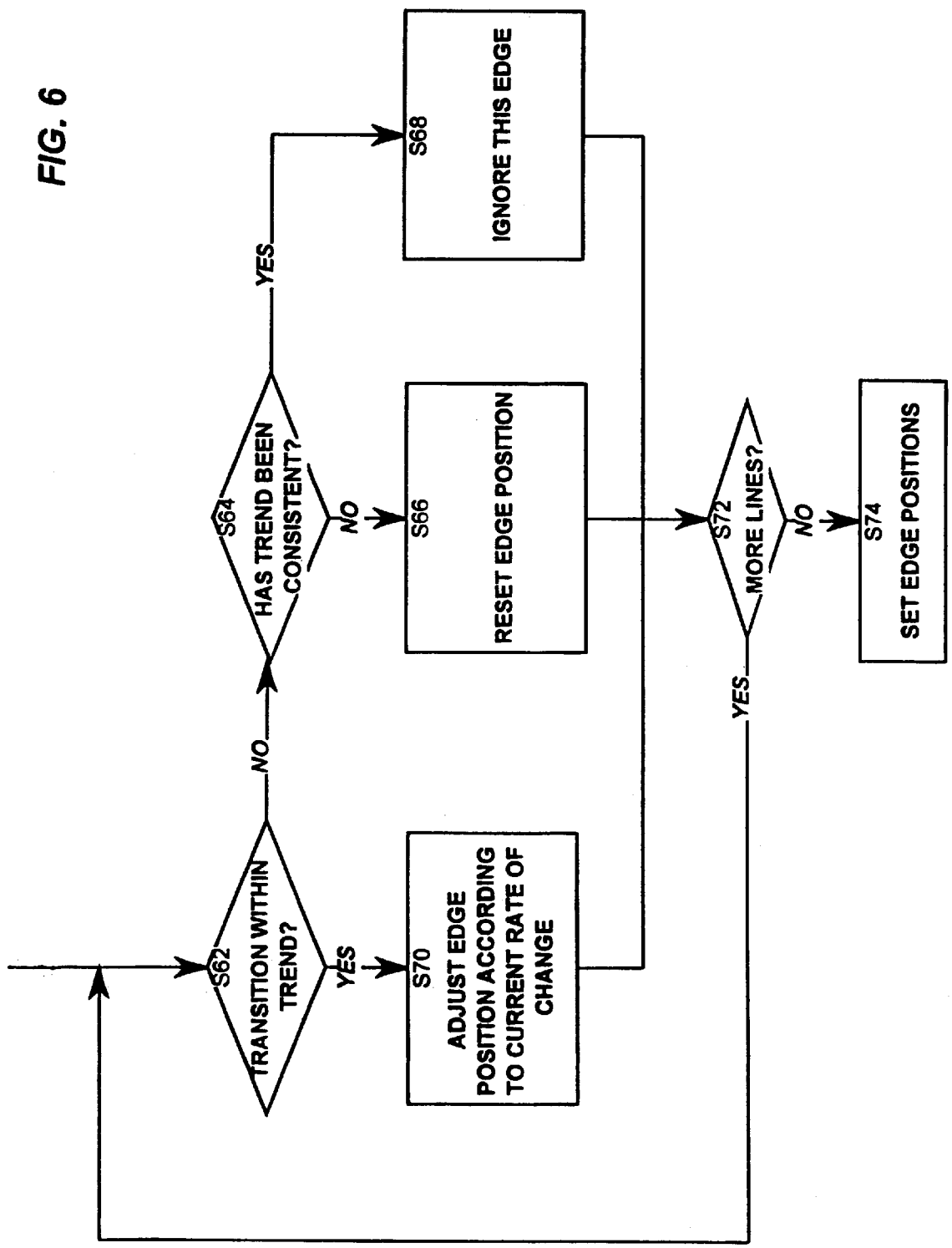
Figure 7:
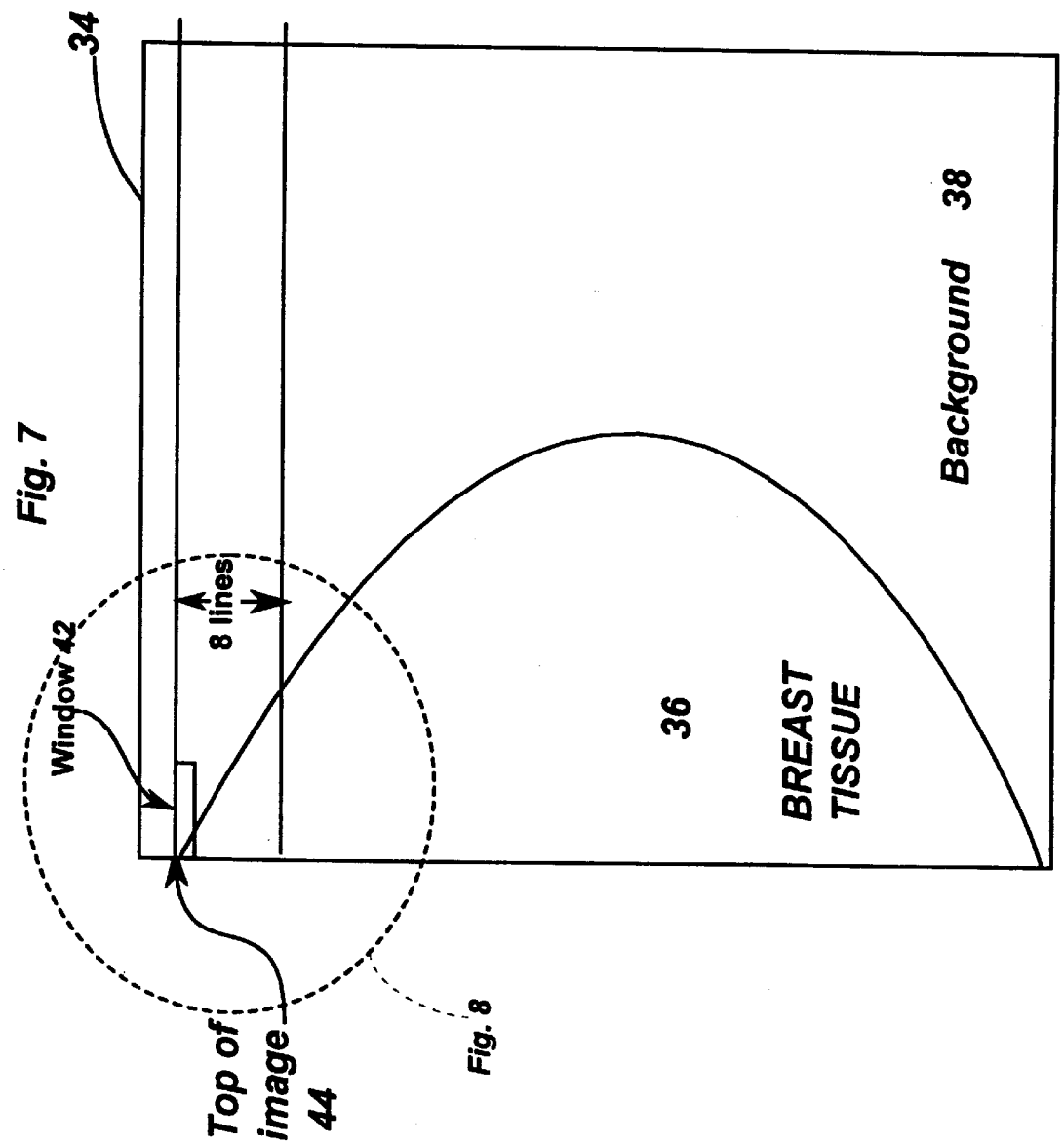
FIGS. 7 and 8 demonstrate aspects of the segmentation process.
Figure 8:
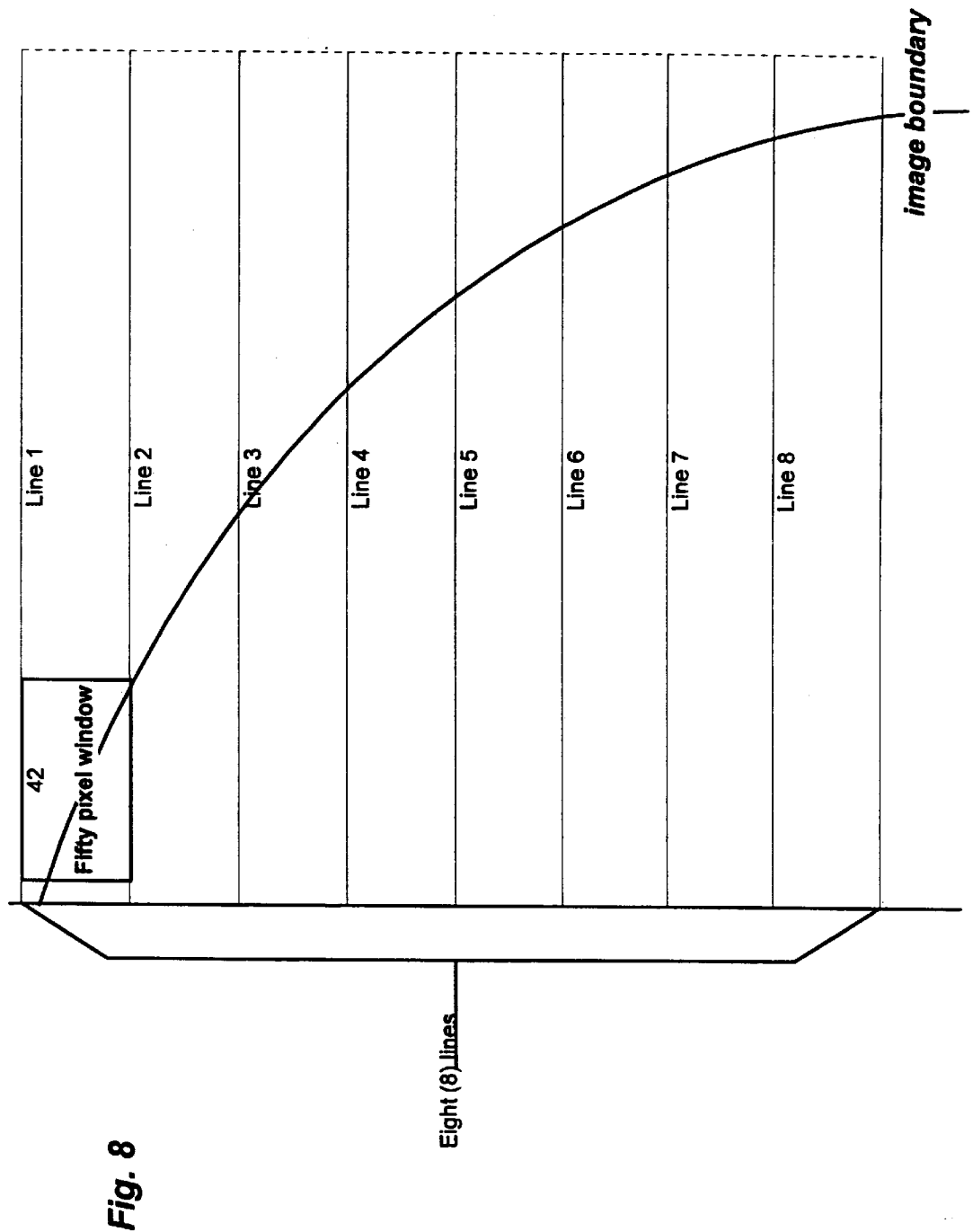

A practitioner can then view the image and perform any appropriate diagnosis. The image processor 26 at the diagnosis site can also perform CAD on the image and display these results on the image display 30, The segmentation step at the remote site 12 is now described in greater detail with reference to FIGS. 5 and 6. Two independent segmentation schemes are included.

Segmentation scheme 1

The first segmentation scheme relies on the fact that x-ray images, radiographs in general and mammograms in particular, have the highest intensity of absorbed x-ray photons just beyond the tissue boundary (that is, the skin line).

Accordingly, if one searches for changes in digital values (that are proportional to signal intensity) along a data line that crosses from tissue to non-tissue areas, then the maximum signal will be just outside the skin line. This is because it contains an area of full direct exposure (that is, no tissue to attenuate primary x-rays) and also scatter radiation from the near tissue.

Figure 9A:
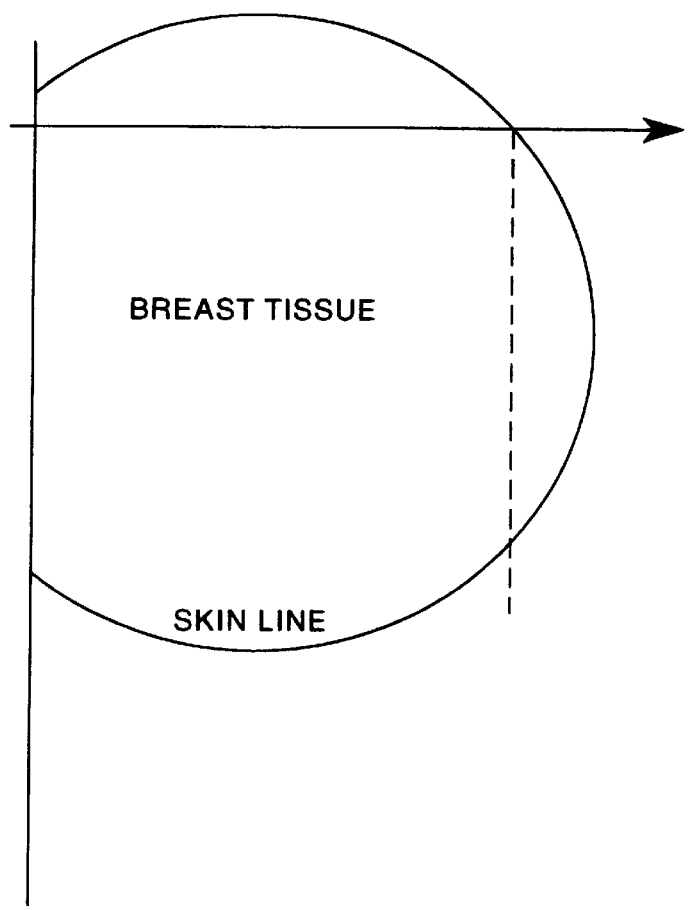
FIGS. 9A and 9B depict a signal line across the image which demonstrates the digital values changing near the skin line, enabling efficient image segmentation according to the present invention.
Figure 9B:
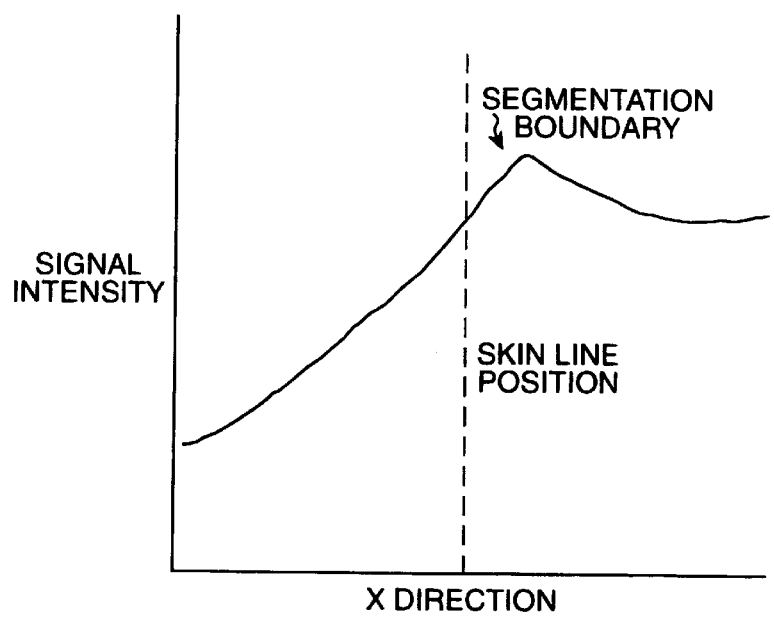

FIGS. 9A–9B depict one such signal line. This maximum signal location can be used as an indication for the segmentation location.

With data from several lines of an input (digitized) image, a continuous smoothed line of segmentation with appropriate shape (for example, convexity) can be constructed on the fly as image data arrives from the acquisition device.

Segmentation scheme 1 operates as follows (with reference to FIGS. 5–8):

First, the top edge 44 (FIG. 7) of the digitized image 34 is located (step S50). This is done by scanning each successive line of the image (starting with the first line) for pixels within lower and upper thresholds until possible image data is found.

The film digitizer 20 with an appropriate lookup table produces twelve-bit values (in the range 0 to 4,095) for the optical density (OD) of each pixel. Presently preferred lower and upper threshold values are 500 and 3100, respectively. These values have been conservatively chosen based on experience with the digitizer (a Lumisys FD 150 in one preferred embodiment) and film (MIN-R) used.

Once the top of the image 44 is found (in step S50), groups of lines (eight lines to a group) are scanned for transition locations (step S52). This is done by using a sliding window 42 (FIGS. 7 and 8) (of size 1×50 pixels) for each line in the group and determining whether the pixels in the window are image pixels. The determination is based on the relative number of pixels within (and outside) the threshold limits described above.

Thus, for each line of the current group (or block) of eight lines, the window is shifted one pixel at a time and each pixel in the window is compared to the threshold values. If more than a certain percentage (75% in preferred embodiments) of the pixels are within the image thresholds, the window is shifted and the percentage is re-calculated. This is repeated until a supposed boundary is located for that line. Since the window is shifted one pixel at a time, it is only necessary to evaluate each pixel once. After the first evaluation, by keeping track of the values of the end pixels of the window, the percentage is easily and quickly recalculated. This is done by determining a total once and then keeping a running total as follows: add 1 for a pixel within the limits and subtract 1 for a pixel outside the limits.

At the end of this process, eight left and right edge candidate pixels have been found, one for each line in the current block.

Next, the left and right edges of the image for the current block (eight lines) are determined (step S54). This determination is made using the process described in FIG. 6 which assesses whether the left and right edges follow a trend within the image.

First, the leftmost and rightmost boundaries of the eight lines in the block are selected as candidates for the left and right edges of the image. Then it is determined whether the edge candidates follow the current trend of the edge (based on previous blocks) (step S62). If the current edge does not follow the trend, then it is determined whether the trend has been consistent (step S64), and if so this edge is ignored (step S68) as an anomaly. That is, if the edge position has been generally smooth and consistent for a number of blocks, do not reset the edge position on widely varying transition locations. If the edge trend has not been consistent (such as when too few blocks have been evaluated to establish a trend) (step S64), then the edge position is reset to the current edge (step S66) and the trend is reset.

If the transition is within the trend (step S62), then the current edge position is adjusted according to the current rate of change of the trend (step S70). That is, if the edge position is close to the last edge position, increase or decrease the edge position by an amount related to the current rate of change of the edge.

The above process is repeated for each line in the block (step S72), at the end of which the edges for this block are set (step S74).

Once the left and right edges for a block have been determined (step S54), extra pixels are added to the edge position (currently 150 pixels) (step S56) to reduce the possibility of error.

The bounds and length of this image block are then provided to the compression routine (steps S58, S30) for compression. The preferred compression technique uses a discrete cosine transformation, quantization and Huffman encoding as in the extended baseline method of the JPEG standard.

This process is repeated for all blocks until the entire image has been processed (step S60).

Segmentation scheme 2

The second segmentation scheme searches for a transition point by counting the number of very high value pixels (above a defined threshold) in a limited range of a line. For example, if five of ten pixels on a line have a digital value over 3,100. This region, in either consecutive or sequential lines, is then smoothed and appropriate convexity is assured. After several segments are done (e.g., the first fifty to five hundred lines of the image), the system predicts (by extending the estimated segmentation line) where the region of interest (suspected segmentation line) in the next line and performs the search for high density value pixels in a limited range of a line.

Finally, the results of the two independent schemes are compared and the disagreements are smoothed (averaged) in order to optimize the final segmentation line. Differences larger than a predetermined value between the two schemes trigger a separate assessment of the optimal segmentation in that region.

The segmented compressed image and associated information (ROIs, patient information etc.) are then transmitted via communications device 18 to a diagnosis site 14 (step S32).

The process of on-the-fly processing above has been described in a linear, sequential manner However, in preferred embodiments, the digitization, segmentation, compression and transmission can be performed in a pipelined fashion as shown in the following table (wherein "D" represents digitization, "S" segmentation, "C" compression and "T" transmission):

| 7 | 6 | 5 | 4 | 3 | 2 | 1 |
|---|---|---|---|---|---|---|
| D | S | C | T |   |   |   |
|   | D | S | C | T |   |   |
|   |   | D | S | C | T |   |
|   |   |   | D | S | C | T |

Each column of this table represents a portion of the image being processed. The first block, no. 1, has already been digitized, segmented and compressed, and needs only to be transmitted. The second block, no. 2, is still being compressed, the third block, no. 3, is still being segmented and the fourth block, no. 4, is still being digitized.

Note that each of these four processes, digitizing, segmenting and compression, takes a different amount of time for a particular block. Accordingly, the first three processes may need to store intermediate results while waiting for a subsequent process (in particular transmittal) to be ready.

Typically the transmitter waits for the segmentation and compression initially, until a significant amount of data has been processed. In a steady state, the segmentation and compression supply data faster than the transmission rate and the compressed data must be stored.

Figure 10A:
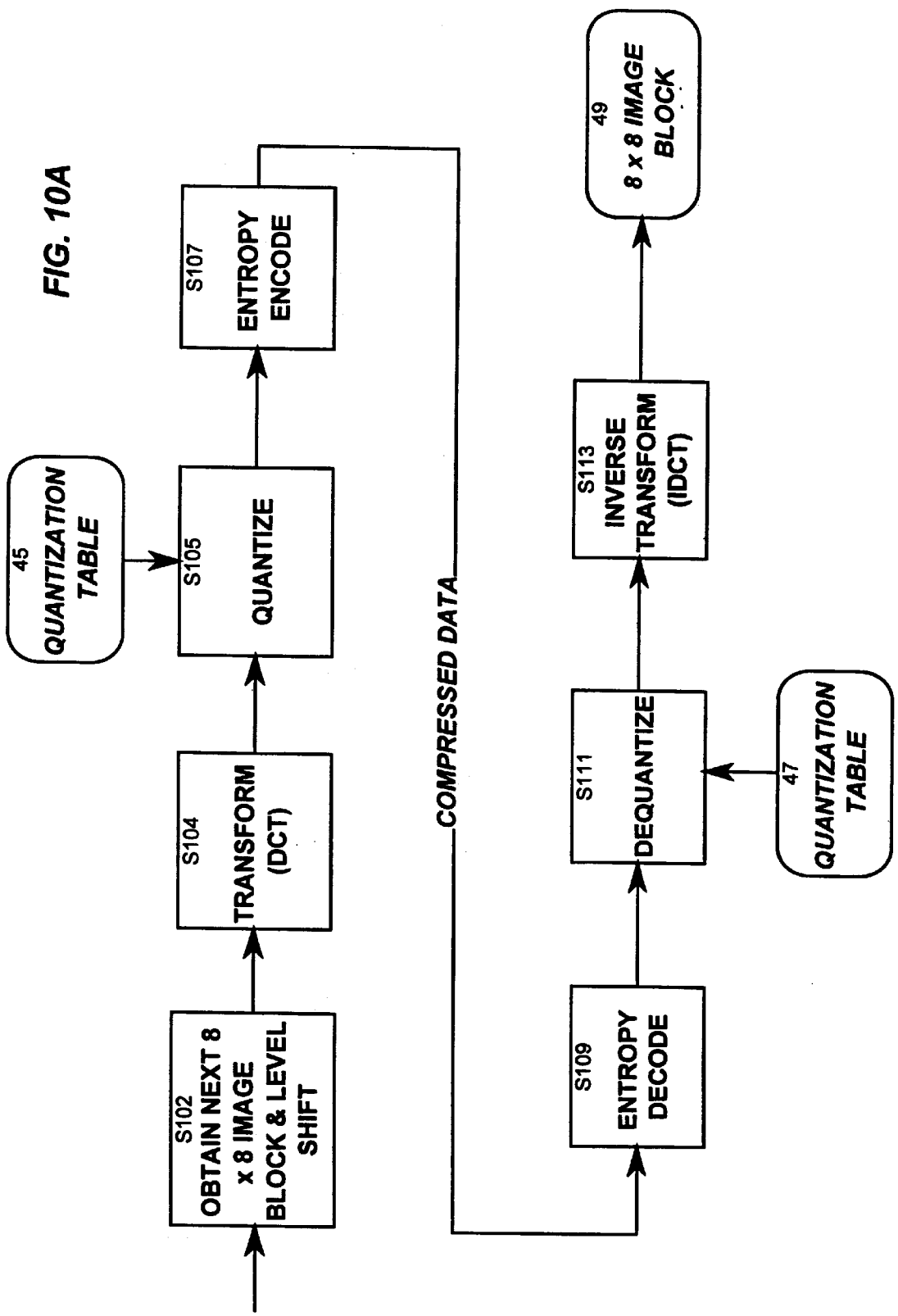
FIG. 10A is a flow chart depicting data compression according to the JPEG algorithm used by the present invention.
Figure 10B:
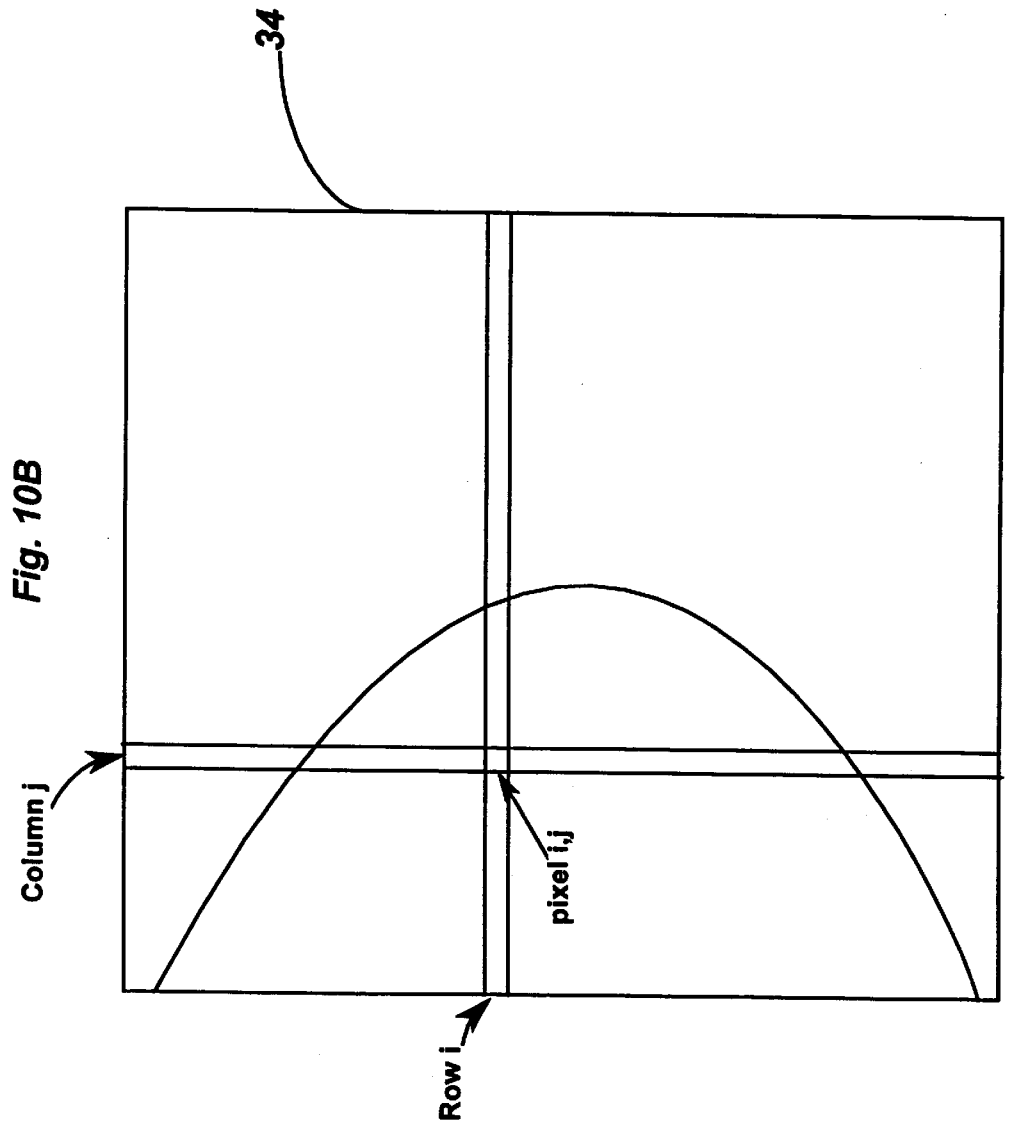
FIGS. 10B and 10C depict aspects of determining a quantization table according to the present invention.

Note that a block of data sent by the transmitter has no relation to a block of eight lines used by the compression. Image quality The present invention uses a JPEG compression algorithm. As shown in FIG. 10A, the JPEG algorithm operates as follows. An input image is processed by partitioning it into one or more sub-regions or blocks. Preferably the sub-regions are 8×8 pixel blocks. While there are still unprocessed image blocks, the next image block is obtained from the image (step S102) and the pixel values are level-shifted. The image block is then transformed to the frequency domain (step S104). This transform is performed using a linear transform such as a Fourier or Cosine transform. The output of such a transform is an array of frequency coefficients for the subregion. JPEG uses the Discrete Cosine Transform (DCT) and produces an 8×8 array of frequency coefficients for each block. The DCT transformed block is then quantized (step S105) using a quantization table 45 of quantization factors. The quantization factors are intended to weight frequency coefficients according to their relative importance (according to some measure of importance). JPEG uses an 8×8 array of quantization factors, one for each frequency coefficient. During the quantization step (S105), the JPEG algorithm essentially divides each frequency coefficient by its corresponding quantization factor and then truncates the result to an integer value.

After quantizing (step S105), each block is entropy encoded (step S107) to produce a block of compressed data. Entropy encoding consists of encoding the quantized frequency coefficients in a reversible manner to minimize the number of bits used to represent the data. JPEG uses either a form of Huffman encoding or a process called adaptive arithmetic encoding.

The compressed data is uncompressed by the inverse process. First it is entropy decoded (step S109), after which it is de-quantized (step S111) using a quantization table 47 (which is usually the same as quantization table 45 used to quantize the block in step S105). The de-quantized block is then inverse transformed (IDCT) (step S113) to produce an 8×8 image block.

The 8×8 image blocks produced in step S113 are reassembled to form the decompressed image.

The JPEG algorithm allows for modification of the quantization tables 45 and 47. As noted above, during the quantization step (S105), the JPEG algorithm essentially divides each frequency coefficient by its corresponding quantization factor and then truncates the result to an integer value. This step causes loss of information during the compression process. The present invention determines these quantization factors (as described below) based on the contrast sensitivity function (CSF) for human vision and on the modulation transfer functions (MTF) of the digitizer used to produce the digitized image and on the device (e.g., a printer) used to output or display the image.

Based on Human Visual System (HVS) modeling, and because different frequencies in the image are preferentially more or less visible to the human eye, the preferred quantization table is modified to match the HVS contrast sensitivity in such a manner that visual "degradation," (if any) appears equal in all frequencies of interest. Because of this optimization protocol, the decompressed image looks and "feels" as much as possible like the original image. The optimization routine depends on the type of image one compresses, hence, the sizes of the objects that may be of interest (i.e., clustered microcalcifications or masses), the digitization resolution (pixel size), and expected viewing distances.

The inventors' model predicts that beyond a specific viewing distance (e.g., greater than fifteen cm for mammograms digitized at 50 μm pixel size), the viewing distance has little effect on the optimal quantization tables in the compression scheme, as is described in more detail below.

The JPEG compression algorithm requires that quantization tables which are suitable for each particular application be specified. The inventors have developed a unique method for generating these tables which is based on the contrast sensitivity function (CSF) of the human visual system as well as on a consideration of losses in high frequency information incurred during digitization and printing. The overall goal of the present quantization strategy is to balance the errors across frequency bands in such a way that the visible errors in each frequency band are approximately equal at all viewing distances greater than some minimum distance (e.g., 15 cm for 50 μm pixel size).

The quantization array required by the JPEG algorithm can be represented as $q_{ij}$ for $0 \leq i, j \leq 7$, where the coefficient $q_{00}$ is the DC component and $q_{77}$ corresponds to the highest two-dimensional frequency. Each quantization value is calculated as the product of three factors times a constant, $$q_{ij} = \frac{1}{CSF(f_i, f_j)} \times MTF_{digitizer}(g_i, g_j) \times MTF_{printer}(g_i, g_j) \times Const$$

Figure 10C:
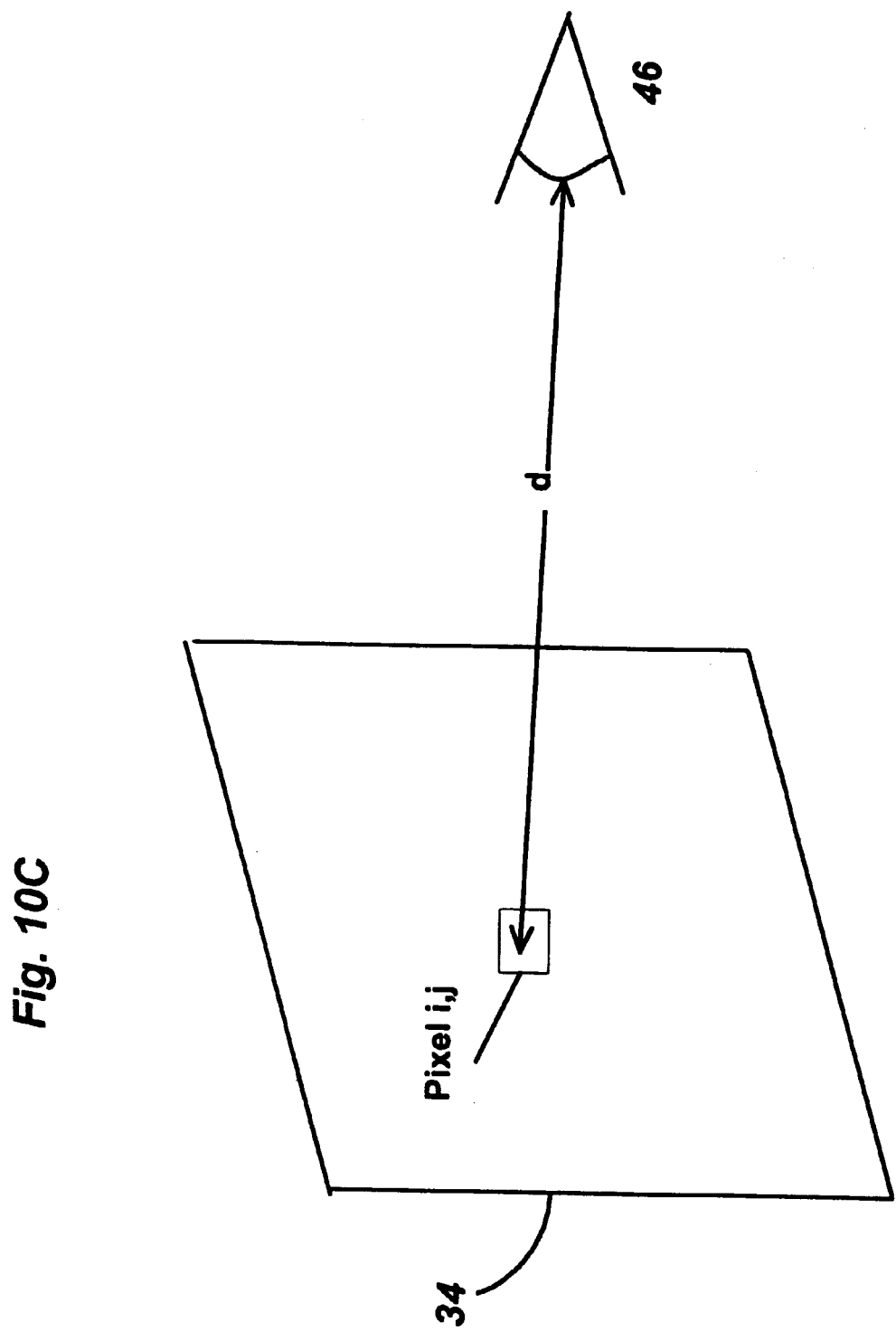

The first factor, $1/(CSF(f_i, f_j))$, relates to the two dimensional contrast sensitivity function (CSF) of the human visual system, where frequencies $f_i$ and $f_j$ are radial frequencies, measured in cycles per degree as seen by an observer at a distance d (see FIG. 10C), and in general $f_k=(k+1)\pi d/2880p$. The second and third factors correspond to the two dimensional modulation transfer functions (MTF) of the digitizer and printer, respectively, with $g_i$ and $g_j$ measured in line pairs per unit length and $g_k=(k+1)/16\,p$ for pixel size p. The MTF of the printer may be replaced by the MTF of any other display device intended to be used, e.g., the MTF of the display monitor 30.

Figure 11:
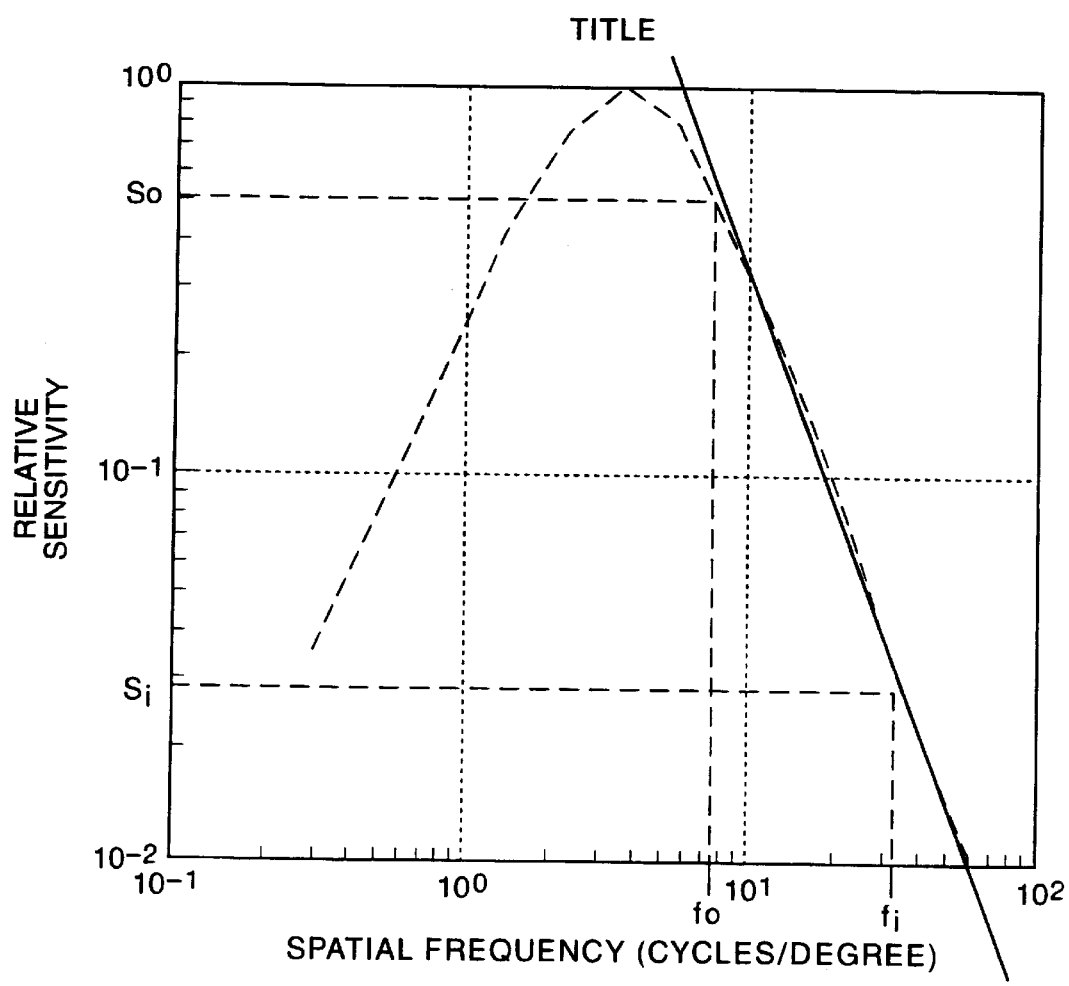
FIG. 11 is a graph depicting a contrast sensitivity function of the human visual system.

Because $f_i$ and $f_j$ depend on the viewing distance d, $CSF(f_i, f_j)$ depends on d, and in general $q_{ij}$ will depend on d. However, the ratios $r_{ij}=q_{ij}/q_{00}$ are essentially independent of d for distances greater than some minimum. As can be seen from the plot of the one-dimensional CSF (FIG. 11), the CSF is approximately linear on a log-log plot for frequencies greater than about 5 cycles/degree. For an 8×8 pixel block, which gives the lowest frequency that can be directly influenced by the quantization process, this corresponds to a viewing distance of greater than 15 cm for an image with 50 μm pixel size. Since $f_i$ is always (i+1) times $f_0$, the distance between $f_0$ and $f_i$ along the frequency axis is independent of d. As long as both $f_0$ and $f_i$ are on the linear part of the CSF, their reflections $s_0$ and $s_i$ on the sensitivity axis will be separated by a constant distance, implying that $s_0/s_i$ is constant. This can be extended to an approximation of the two-dimensional CSF to show that $CSF(f_0,f_0)/CSF(f_i,f_j)$ is essentially independent of d for $f_i$, $f_j$>5 cycles/degree. Thus, for sufficiently large d, $r_{ij}=q_{ij}/q_{00}$ is independent of d.

The quantization table is calculated for the CSF and MTFs by calculating a matrix of ratios $r_{ij}$ for the viewing distance corresponding to the linear part of the CSF curve, and then multiplying that matrix by a constant which has been chosen to give the desired compression ratio.

The CSF along with the MTFs of the printer and digitizer provide all of the data required in order to calculate quantization tables with the desired properties. This optimization routine depends on the type of image one compresses, hence, the sizes of the objects that may be of interest (i.e., clustered microcalcifications or masses), the digitization resolution, pixel size, and expected viewing distances. However, as it turns out, our model predicts that beyond a specific viewing distance (e.g., fifteen centimeters (15 cm) for mammograms digitized at 50 μm pixel size), the viewing distance has little effect on the optimal quantization tables in the compression scheme.

Since the model predicts that most, if not all, frequencies in question are on the side of the sensitivity curve where linearity between log frequency and relative contrast sensitivity can be assumed, the quantization tables in the compression are set to allow for the same ratio of contrast to appear on the decompressed image for the frequencies in question (erg., DC and 20 lp/mm).

Experiments in both breast and chest imaging have clearly demonstrated that a variety of quantization and processing schemes using this approach consistently results in decompressed images that are selected by observers as being visibly closest to the original, noncompressed image.

In an experiment of the overall system using over one hundred images, the total cycle time (end-to-end, excluding CAD) averaged less than four minutes per image.

Thus, a system for telemammography with real-time image segmentation is provided. One skilled in the art will appreciate that the present invention can be practiced by other than the described embodiments, which are presented for purposes of illustration and not limitation, and the present invention is limited only by the claims that follow.

What is claimed:

1. A method for transmitting a radiograph to a diagnosis location from a remote location, the method comprising, at the remote location:

obtaining and digitizing a radiographic image containing a tissue image portion and a background image portion, wherein the image can be considered to comprise a plurality of blocks;

segmenting a block of the plurality of blocks of the digitized radiographic image to obtain a part of the block which corresponds to said tissue image portion;

compressing and transmitting the part of the block to the diagnosis location; and repeating the segmenting, compressing and transmitting of blocks until the entire tissue image portion has been transmitted to the diagnosis location.

2. A method as in claim 1, further comprising, at the remote location:

optionally performing computer assisted diagnosis (CAD) on the digitized image; and transmitting the results of the CAD to the diagnosis location.

3. A method as in claim 2, further comprising, at the diagnosis location:

receiving the compressed segmented image and the CAD results;

uncompressing the received image;

combining the CAD results with the uncompressed image; and displaying the uncompressed image and the CAD results.

4. A method as in claim 1, wherein the segmenting of the image comprises:

applying a first segmentation scheme to the image;

applying a second segmentation scheme, independent of said first segmentation scheme, to the image; and comparing results of the first and second segmentation schemes to obtain a final segmentation of the image.

5. A method as in claim 1, further comprising, at the remote location:

finding and extracting identification information from the image prior to segmenting the image; and transmitting the identification information to the diagnosis location; and, at the diagnosis location, receiving the identification information from the remote location; and adding the identification information back to the uncompressed image.

6. A method as in claim 5, further comprising, at the remote location:

computing a digital signature of the image; and transmitting the digital signature of the image to the diagnosis location; and, at the diagnosis location, receiving and checking the digital signature to determine if the image is valid.

7. A method as in claim 6 wherein the digital signature is determined based on the parts of the blocks of the digitized image that depict mainly tissue and on the identification information.

8. A method for transmitting a radiograph to a diagnosis location from a remote location, the method comprising, at the remote location:

obtaining and digitizing a radiographic image containing a tissue image portion and a background image portion, wherein the image can be considered to comprise a plurality of blocks;

segmenting a block of the plurality of blocks of the digitized radiographic image to obtain a part of the block which corresponds to said tissue image portion;

compressing and transmitting the part of the block to the diagnosis location; and repeating the segmenting, compressing and transmitting of blocks until the entire tissue image portion has been transmitted to the diagnosis location, and, at the diagnosis location:

receiving the compressed segmented image;

uncompressing the received image; and during compression, quantizing frequency coefficients based on a quantization table, the quantization table being based on a contrast sensitivity function (CSF) of the human visual system as well as on losses in information incurred during digitizing and displaying the image.

9. A method as in claim 8, wherein each quantization coefficient value of the quantization table is calculated as the product of a constant times three factors, where the first factor relates to the two-dimensional CSF, and the second and third factors correspond to two-dimensional modulation transfer functions (MTF) of a digitizer used in the digitizing of the image and a device used to display the image, respectively.

10. A method as in claim 9, wherein the first factor for each coefficient value $q_{ij}$ is determined by the formula:

$$\frac{1}{CFS(f_i, f_j)},$$

where $f_i$ and $f_j$ are the horizontal and vertical radial frequencies calculated as $$f_x = \frac{(x+1)\pi d}{8 \times 360 p},$$

where d is a minimum expected viewing distance to the image and p is a pixel size of the image.

11. A method as in claim 10, wherein the second and third factors are functions of image frequencies measured in line pairs per unit length.

12. A system for transmitting a radiograph from a remote site to a diagnosis site, the system comprising a remote site connectable to the diagnosis site,
   the remote site comprising:
   (a) means for obtaining and digitizing a radiographic image containing a tissue image portion and a background image portion, wherein the image can be considered to comprise a plurality of blocks;
   (b) means for segmenting a block of the plurality of blocks of the digitized radiographic image to obtain a part of the block which corresponds to said tissue image portion;
   (c) means for compressing and transmitting the part of the block to the diagnosis site; and
   (d) means repeating the segmenting, compressing and transmitting of blocks until the entire tissue image portion has been transmitted to the diagnosis site.

13. A system as in claim 12, wherein the remote site further comprises:
   means for optionally performing computer assisted diagnosis (CAD) on the digitized image; and
   means transmitting the results of the CAD to the diagnosis site.

14. A system as in claim 13, further comprising, at the remote location:
   means for finding and extracting identification information from the image; and
   means for transmitting the identification information to the diagnosis site, and, at the diagnosis site,
   means for receiving the identification information from the first location; and
   means for adding the identification information back to the uncompressed image.

15. A system as in claim 14, further comprising, at the remote location, means for computing a digital signature of the image; and
means for transmitting the digital signature of the image to the diagnosis site, and wherein the diagnosis site further comprises:
means for receiving and checking the digital signature to determine if the image is valid.

16. A system as in claim 15, wherein the digital signature is determined based on the parts of the blocks of the digitized image that depict mainly tissue and on the identification information.

17. A system as in claim 12 wherein the diagnosis site comprises:
   (a) means for receiving the compressed segmented image and the CAD results;
   (b) means for uncompressing the received image;
   (c) means for combining the CAD results with the uncompressed image; and
   (d) means for displaying the uncompressed image and the CAD results.

18. A system as in claim 17, wherein the means for segmenting the image further comprises:
   means for applying a first segmentation scheme to the image;
   means for applying a second segmentation scheme, independent of said first segmentation scheme, to the image; and
   means comparing results of the first and second segmentation schemes to obtain a final segmentation of the image.

19. A system for transmitting a radiograph from a remote site to a diagnosis site, the system comprising a remote site connectable to the diagnosis site, the diagnosis site comprising:
   (a) means for receiving a compressed segmented image;
   (b) means for uncompressing the received image;
   (c) means for quantizing frequency coefficients based on a quantization table, the quantization table being based on a contrast sensitivity function (CSF) of the human visual system as well as on losses in information incurred during digitizing the image,
   wherein each quantization coefficient value $q_{ij}$ of the quantization table is calculated as the product of a constant times three factors, where the first factor relates to the two-dimensional CSF and the second and third factors correspond to two-dimensional modulation transfer functions (MTF) of a digitizer used in digitizing the image and a device used to output the image, respectively, wherein the first factor for each value $q_{ij}$ is determined by the formula:

$$\frac{1}{CFS(f_i, f_j)},$$

where $f_i$ and $f_j$ are the horizontal and vertical radial frequencies at location (i, j), calculated as $$f_x = \frac{(x+1)\pi d}{8 \times 360 p},$$

where d is a minimum expected viewing distance to the image and p is a pixel size of the image.

20. A system for transmitting a radiograph from a remote site to a diagnosis site, the system comprising a remote site connectable to the diagnosis site, the diagnosis site comprising:

(a) means for receiving a compressed segmented image;
(b) means for uncompressing the received image;
(c) means for quantizing frequency coefficients based on a quantization table, the quantization table being based on a contrast sensitivity function (CSF) of the human visual system as well as on losses in information incurred during digitizing the image, wherein each quantization coefficient value $q_{ij}$ of the quantization table is calculated as the product of a constant times three factors, where the first factor relates to the two-dimensional CSF, and the second and third factors correspond to two-dimensional modulation transfer functions (MTF) of a digitizer used in digitizing the image and a device used to output the image, respectively, wherein the second and third factors are functions of image frequencies measured in line pairs per unit length.

21. A telemammography network comprising a plurality of remote sites connectable to a diagnosis site, each of said remote sites comprising:

(a) means for obtaining and digitizing a mammographic image containing a part depicting breast tissue and a background part, wherein the image can be considered to comprise a plurality of blocks;

(b) means for segmenting a block of the plurality of blocks of the digitized radiographic image to obtain a part of the block which depicts mainly breast tissue;

(c) means for compressing and transmitting the part of the block; and (d) means repeating the segmenting, compressing and transmitting of blocks to the diagnosis site until the entire part of the image which depicts tissue has been transmitted to the diagnosis site, and the diagnosis site comprising:

(a) means for receiving a compressed segmented image from any one of said remote sites;

(b) means for uncompressing the received compressed segmented image;

(c) means for combining the CAD results with the uncompressed image; and (d) means for displaying the uncompressed image.

22. A method for transmitting a radiograph to a diagnosis location from a remote location, the radiograph having a contrast characteristic, the method comprising, at the remote location:

obtaining and digitizing a radiographic image containing a background image portion and an image portion corresponding to said contrast characteristic, wherein the image can be considered to comprise a plurality of blocks;

segmenting a block of the plurality of blocks of the digitized radiographic image to obtain a part of the block which corresponds to said image portion corresponding to said contrast characteristic;

compressing and transmitting the part of the block to the diagnosis location; and repeating the segmenting, compressing and transmitting of blocks until the entire image portion corresponding to said contrast characteristic has been transmitted to the diagnosis location.

23. A method as in claim 22, wherein said contrast characteristic determines a tissue portion of said image.

24. A system for transmitting a radiograph to a diagnosis location from a remote location, the radiograph having a contrast characteristic, the system comprising, at the remote location:

means for obtaining and digitizing a radiographic image containing a background image portion and an image portion corresponding to said contrast characteristic, wherein the image can be considered to comprise a plurality of blocks;

means for segmenting a block of the plurality of blocks of the digitized radiographic image to obtain a part of the block which corresponds to said image portion corresponding to said contrast characteristic;

means for compressing and transmitting the part of the block to the diagnosis location; and means for repeating the segmenting, compressing and transmitting of blocks until the entire image portion corresponding to said contrast characteristic has been transmitted to the diagnosis location.

25. A system as in claim 24, wherein said contrast characteristic determines a tissue portion of said image.

26. A quantization table for use during compression of a part of an image, the quantization table being based on a contrast sensitivity function (CSF) of the human visual system as well as on losses in information incurred during digitizing the image, wherein each quantization coefficient value of the quantization table is the product of a constant times three factors, where the first factor relates to the two-dimensional CSF, and the second and third factors correspond to two-dimensional modulation transfer functions (MTF) of a digitizer used in the digitizing of the image and a printer used to print the image, respectively, wherein the first factor for each coefficient value $q_{ij}$ is determined by the formula:

$$\frac{1}{CFS(f_i, f_j)},$$

where $f_i$ and $f_j$ are the horizontal and vertical radial frequencies at location (i, j), calculated as $$f_x = \frac{(x+1)\pi d}{8 \times 360 p},$$

where d is a minimum expected distance to the image and p is a pixel size of the image.

27. A quantization table for use during compression of a part of an image, the quantization table being based on a contrast sensitivity function (CSF) of the human visual system as well as on losses in information incurred during digitizing the image, wherein each quantization coefficient value of the quantization table is the product of a constant times three factors, where the first factor relates to the two-dimensional CSF, and the second and third factors correspond to two-dimensional modulation transfer functions (MTF) of a digitizer used in the digitizing of the image and a printer used to print the image, respectively, wherein the second and third factors are functions of image frequencies measured in line pairs per unit length.

28. A method of determining a quantization table for use during compression of a part of an image, the quantization table being based on a contrast sensitivity function (CSF) of the human visual system as well as on losses in information incurred during digitizing the image, the method comprising determining each quantization coefficient value of the quantization table as the product of a constant times three factors, where the first factor relates to the two-dimensional CSF, and the second and third factors correspond to two-dimensional modulation transfer functions (MTF) of a digitizer used in the step of digitizing the image and a device used to output the image, respectively, wherein the first factor for each coefficient value $q_{ij}$ is determined by the formula:

$$\frac{1}{s(f_i, f_j)},$$

where $f_i$ and $f_j$ are the horizontal and vertical radial frequencies at location (i, j), calculated as $$f_x = \frac{(x+1)\pi d}{8 \times 360p},$$

where d is a minimum expected viewing distance to the image and p is a pixel size of the image.

29. A method of determining a quantization table for use during compression of a part of an image, the quantization table being based on a contrast sensitivity function (CSF) of the human visual system as well as on losses in information incurred during digitizing the image, the method comprising determining each quantization coefficient value of the quantization table as the product of a constant times three factors, where the first factor relates to the two-dimensional CSF, and the second and third factors correspond to two-dimensional modulation transfer functions (MTF) of a digitizer used in the step of digitizing the image and a device used to output the image, respectively, wherein the second and third factors are functions of image frequencies measured in line pairs per unit length.

30. A method for transmitting a radiograph to a diagnosis location from a remote location, the method comprising, at the remote location:
  (A) obtaining a radiographic image containing a tissue image portion and a background image portion, wherein the image can be considered to comprise a plurality of blocks; and
  (B) repeatedly, until the entire tissue image portion has been transmitted to the diagnosis location,
    (b1) digitizing a block of the plurality of blocks of the radiographic image to produce a digitized block of the radiographic image;
    (b2) segmenting the digitized block of the radiographic image to obtain a part of the block which corresponds to said tissue image portion;
    (b3) compressing the part of the block; and
    (b4) transmitting the compressed part of the block to the diagnosis location.

31. A method as in claim 30, further comprising, at the remote location:
  optionally performing computer assisted diagnosis (CAD) on the digitized image; and
  transmitting the results of the CAD to the diagnosis location.

32. A method as in claim 31, further comprising, at the diagnosis location:
  receiving the compressed segmented image and the CAD results;
  uncompressing the received image;
  combining the CAD results with the uncompressed image; and
  displaying the uncompressed image and the CAD results.

33. A method as in claim 30, wherein the segmenting of the image comprises:

applying a first segmentation scheme to the image;
  applying a second segmentation scheme, independent of said first segmentation scheme, to the image; and
  comparing results of the first and second segmentation schemes to obtain a final segmentation of the image.

34. A method as in claim 30, further comprising, at the remote location:
  finding and extracting identification information from the image prior to segmenting the image; and
  transmitting the identification information to the diagnosis location; and, at the diagnosis location,
  receiving the identification information from the remote location; and
  adding the identification information back to the uncompressed image.

35. A method as in claim 34, further comprising, at the remote location:
  computing a digital signature of the image; and
  transmitting the digital signature of the image to the diagnosis location; and, at the diagnosis location,
  receiving and checking the digital signature to determine if the image is valid.

36. A method as in claim 35 wherein the digital signature is determined based on the parts of the blocks of the digitized image that depict mainly tissue and on the identification information.

37. A method for transmitting a radiograph to a diagnosis location from a remote location, the method comprising, at the remote location:
  (A) obtaining a radiographic image containing a tissue image portion and a background image portion, wherein the image can be considered to comprise a plurality of blocks; and
  (B) repeatedly, until the entire tissue image portion has been transmitted to the diagnosis location,
    (b1) digitizing a block of the plurality of blocks of the radiographic image to obtain a digitized block of the radiographic image;
    (b2) segmenting the digitized block of the radiographic image to obtain a part of the block which corresponds to said tissue image portion;
    (b3) compressing and transmitting the part of the block to the diagnosis location; and,
  at the diagnosis location:
  (C) receiving the compressed segmented image;
  (D) uncompressing the received image; and
  (E) during compression, quantizing frequency coefficients based on a quantization table, the quantization table being based on a contrast sensitivity function (CSF) of the human visual system as well as on losses in information incurred during digitizing and displaying the image.

38. A method as in claim 37, wherein each quantization coefficient value of the quantization table is calculated as the product of a constant times three factors, where the first factor relates to the two-dimensional CSF, and the second and third factors correspond to two-dimensional modulation transfer functions (MTF) of a digitizer used in the digitizing of the image and a device used to display the image, respectively.

39. A method as in claim 38, wherein the first factor for each coefficient value $q_{ij}$ is determined by the formula:

$$\frac{1}{CFS(f_i, f_j)},$$

where $f_i$ and $f_j$ are the horizontal and vertical radial frequencies calculated as $$f_x = \frac{(x+1)\pi d}{8 \times 360 p},$$

where d is a minimum expected viewing distance to the image and p is a pixel size of the image.

40. A method as in claim 39, wherein the second and third factors are functions of image frequencies measured in line pairs per unit length.

41. A system for transmitting a radiograph from a remote site to a diagnosis site, the system comprising a remote site connectable to the diagnosis site,
the remote site comprising:
  (a) means for obtaining a radiographic image containing a tissue image portion and a background image portion, wherein the image can be considered to comprise a plurality of blocks;
  (b) means for digitizing a block of the plurality of blocks of the radiographic image to produce a digitized block of the image;
  (c) means for segmenting the digitized block of the radiographic image to obtain a part of the block which corresponds to said tissue image portion;
  (d) means for compressing and transmitting the part of the block to the diagnosis site; and
  (e) means for repeating the digitizing, segmenting, compressing and transmitting of blocks until the entire tissue image portion has been transmitted to the diagnosis site.

42. A system as in claim 41, wherein the remote site further comprises:
  means for optionally performing computer assisted diagnosis (CAD) on the digitized image; and
  means transmitting the results of the CAD to the diagnosis site.

43. A system as in claim 42, further comprising, at the remote location:
  means for finding and extracting identification information from the image; and
  means for transmitting the identification information to the diagnosis site, and, at the diagnosis site,
  means for receiving the identification information from the first location; and
  means for adding the identification information back to the uncompressed image.

44. A system as in claim 43, further comprising, at the remote location,
  means for computing a digital signature of the image; and
  means for transmitting the digital signature of the image to the diagnosis site, and wherein the diagnosis site further comprises:
  means for receiving and checking the digital signature to determine if the image is valid.

45. A system as in claim 44, wherein the digital signature is determined based on the parts of the blocks of the digitized image that depict mainly tissue and on the identification information.

46. A system as in claim 41 wherein the diagnosis site comprises:
  (a) means for receiving the compressed segmented image and the CAD results;
  (b) means for uncompressing the received image;
  (c) means for combining the CAD results with the uncompressed image; and
  (d) means for displaying the uncompressed image and the CAD results.

47. A system as in claim 46, wherein the means for segmenting the image further comprises:
  means for applying a first segmentation scheme to the image;
  means for applying a second segmentation scheme, independent of said first segmentation scheme, to the image; and
  means comparing results of the first and second segmentation schemes to obtain a final segmentation of the image.

48. A telemammography network comprising a plurality of remote sites connectable to a diagnosis site, each of said remote sites comprising:
  (a) means for obtaining a mammographic image containing a part depicting breast tissue and a background part, wherein the image can be considered to comprise a plurality of blocks;
  (b) means for digitizing a block of the plurality of blocks of the mammographic image to obtain a digitized block of the mammographic image;
  (b) means for segmenting the digitized block of the mammographic image to obtain a part of the block which depicts mainly breast tissue;
  (c) means for compressing and transmitting the part of the block; and
  (d) means repeating the digitizing, segmenting, compressing and transmitting of blocks to the diagnosis site until the entire part of the image which depicts tissue has been transmitted to the diagnosis site, and the diagnosis site comprising:
  (a) means for receiving a compressed segmented image from any one of said remote sites;
  (b) means for uncompressing the received compressed segmented image;
  (c) means for combining the CAD results with the uncompressed image; and
  (d) means for displaying the uncompressed image.

49. A method for transmitting a radiograph to a diagnosis location from a remote location, the radiograph having a contrast characteristic, the method comprising, at the remote location:
  (A) obtaining a radiographic image containing a background image portion and an image portion corresponding to said contrast characteristic, wherein the image can be considered to comprise a plurality of blocks; and
  (B) repeatedly, until the entire image portion corresponding to said contrast characteristic has been transmitted to the diagnosis location,
    (b1) digitizing a block of the plurality of blocks of the radiographic image to produce a digitized block of the radiographic image;
    (b2) segmenting the digitized block of the radiographic image to obtain a part of the block which corresponds to said image portion corresponding to said contrast characteristic; and
    (b3) compressing and transmitting the part of the block to the diagnosis location.

50. A method as in claim 49, wherein said contrast characteristic determines a tissue portion of said image.

51. A system for transmitting a radiograph to a diagnosis location from a remote location, the radiograph having a contrast characteristic, the system comprising, at the remote location:

means for obtaining a radiographic image containing a background image portion and an image portion corresponding to said contrast characteristic, wherein the image can be considered to comprise a plurality of blocks;

means for digitizing a block of the plurality of blocks of the radiographic image to obtain a digitized block of the radiographic image;

means for segmenting a digitized block of the radiographic image to obtain a part of the block which corresponds to said image portion corresponding to said contrast characteristic;

means for compressing and transmitting the part of the block to the diagnosis location; and means for repeating the digitizing, segmenting, compressing and transmitting of blocks until the entire image portion corresponding to said contrast characteristic has been transmitted to the diagnosis location.

52. A system as in claim 51, wherein said contrast characteristic determines a tissue portion of said image.

53. A method for transmitting a radiograph to a diagnosis location from a remote location, the method comprising, at the remote location:

obtaining a radiographic image containing a tissue image portion and a background image portion, wherein the image can be considered to comprise a plurality of blocks;

digitizing the radiographic image to obtain a digitized radiographic image;

segmenting a block of the digitized radiographic image to obtain a part of the block which corresponds to said tissue image portion;

compressing and transmitting the part of the block to the diagnosis location; and repeating the segmenting, compressing and transmitting of blocks until the entire tissue image portion has been transmitted to the diagnosis location, and, at the diagnosis location:

receiving the compressed segmented image;

uncompressing the received image; and during compression, quantizing frequency coefficients based on a quantization table, the quantization table being based on a contrast sensitivity function (CSF) of the human visual system as well as on losses in information incurred during digitizing and displaying the image, wherein each quantization coefficient value of the quantization table is calculated as the product of a constant times three factors, where the first factor relates to the two-dimensional CSF, and the second and third factors correspond to two-dimensional modulation transfer functions (MTF) of a digitizer used in the digitizing of the image and a device used to display the image, respectively, and wherein the first factor for each coefficient value $q_{ij}$ is determined by the formula:

$$\frac{1}{CFS(f_i, f_j)},$$

where $f_i$ and $f_j$ are the horizontal and vertical radial frequencies calculated as $$f_x = \frac{(x+1)\pi d}{8 \times 360p},$$

where d is a minimum expected viewing distance to the image and p is a pixel size of the image.

54. A method as in claim 53, wherein the second and third factors are functions of image frequencies measured in line pairs per unit length.

55. A quantization table for use during compression of a part of an image, the quantization table being based on a contrast sensitivity function (CSF) of the human visual system as well as on losses in information incurred during digitizing the image, wherein each quantization coefficient value of the quantization table is the product of a constant times three factors, where the first factor relates to the two-dimensional CSF, and the second and third factors correspond to two-dimensional modulation transfer functions (MTF) of a digitizer used in the digitizing of the image and a printer used to print the image, respectively, wherein the first factor for each coefficient value $q_{ij}$ is determined by the formula:

$$\frac{1}{CFS(f_i, f_j)},$$

where $f_i$ and $f_j$ are the horizontal and vertical radial frequencies at location (i, j), calculated as $$f_x = \frac{(x+1)\pi d}{8 \times 360p},$$

where d is a minimum expected distance to the image and p is a pixel size of the image.

56. A method of determining a quantization table for use during compression of a part of an image, the quantization table being based on a contrast sensitivity function (CSF) of the human visual system as well as on losses in information incurred during digitizing the image, the method comprising determining each quantization coefficient value of the quantization table as the product of a constant times three factors, where the first factor relates to the two-dimensional CSF, and the second and third factors correspond to two-dimensional modulation transfer functions (MTF) of a digitizer used in the step of digitizing the image and a device used to output the image, respectively, wherein the first factor for each coefficient value $q_{ij}$ is determined by the formula:

$$\frac{1}{s(f_i, f_j)},$$

where $f_i$ and $f_j$ are the horizontal and vertical radial frequencies at location (i, j), calculated as $$f_x = \frac{(x+1)\pi d}{8 \times 360p},$$

where d is a minimum expected viewing distance to the image and p is a pixel size of the image.

* * * * *